United States Patent [19]

Konoshima

[11] Patent Number: 4,474,419

[45] Date of Patent: Oct. 2, 1984

[54] SOCKET STRUCTURE OF A LIGHT SOURCE UNIT FOR AN ENDOSCOPE SYSTEM

[75] Inventor: Katunaga Konoshima, Tokyo, Japan

[73] Assignee: Olympus Optical Co., Ltd., Tokyo, Japan

[21] Appl. No.: 373,534

[22] Filed: Apr. 30, 1982

[30] Foreign Application Priority Data

May 13, 1981 [JP] Japan ................. 56-71696

[51] Int. Cl.³ .................................. H01R 3/00
[52] U.S. Cl. ............................... 339/147 R
[58] Field of Search ............ 339/90 F, 186 T, 147 R; 128/303.15

[56] References Cited

U.S. PATENT DOCUMENTS 2,951,108 8/1960 Woods ....................... 339/90 F

FOREIGN PATENT DOCUMENTS 765855 3/1934 France ....................... 339/186 T
916928 9/1946 France ....................... 339/186 T Primary Examiner—Eugene F. Desmond

[57] ABSTRACT

A light source unit for an endoscope has a socket to which a plug at the end of a universal code of the endoscope is attached. The socket has a socket body with a recess in which the plug is fitted and socket terminals to which plug terminals are connected. A number of slots opening to the recess are formed in the socket body. The slots extend along the insertion path of the plug terminals and have the socket terminals therein. The socket terminals cannot be directly touched by a finger or the like. When the plug is attached to the socket, the plug terminals come into contact with the socket terminals properly.

4 Claims, 6 Drawing Figures

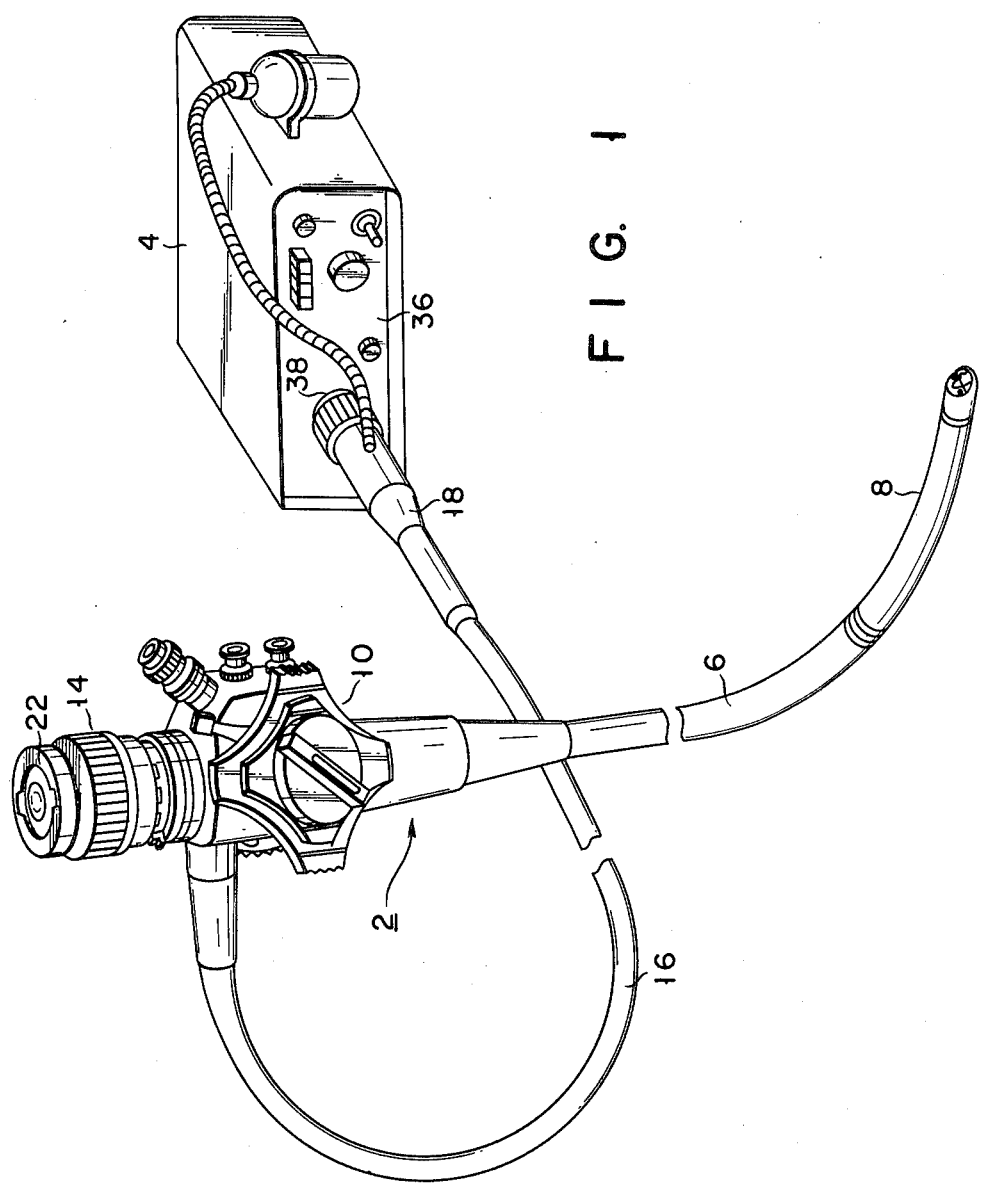

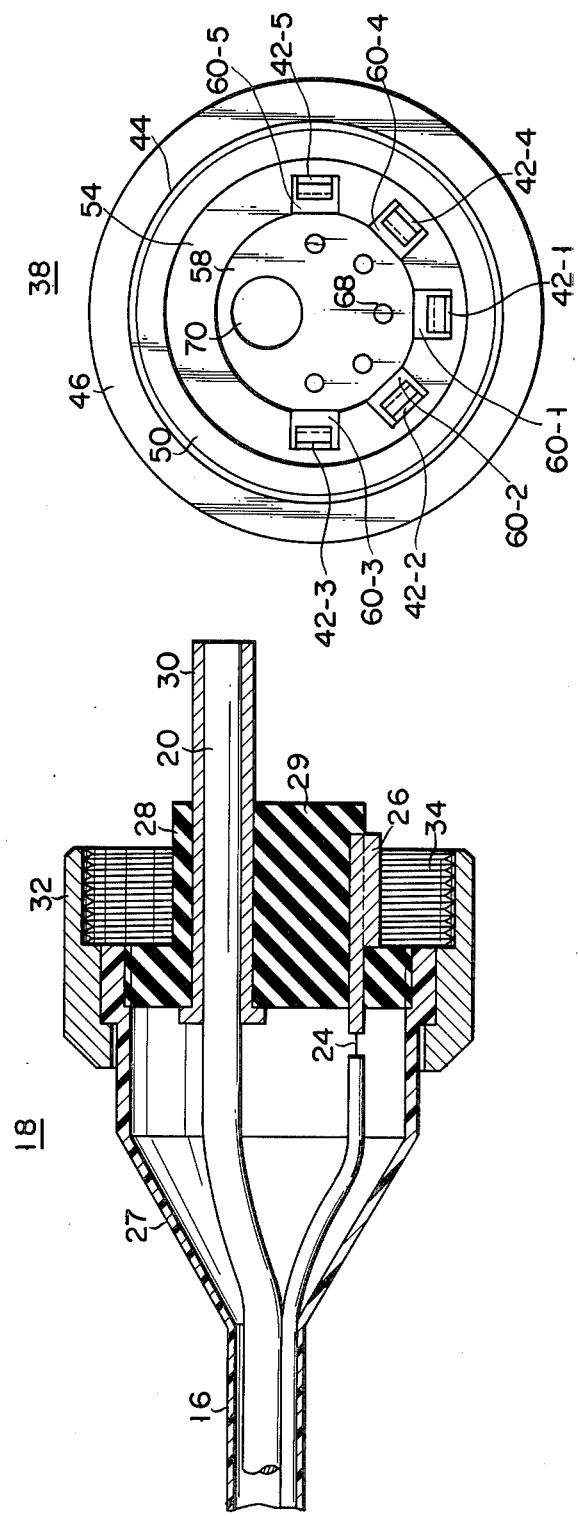

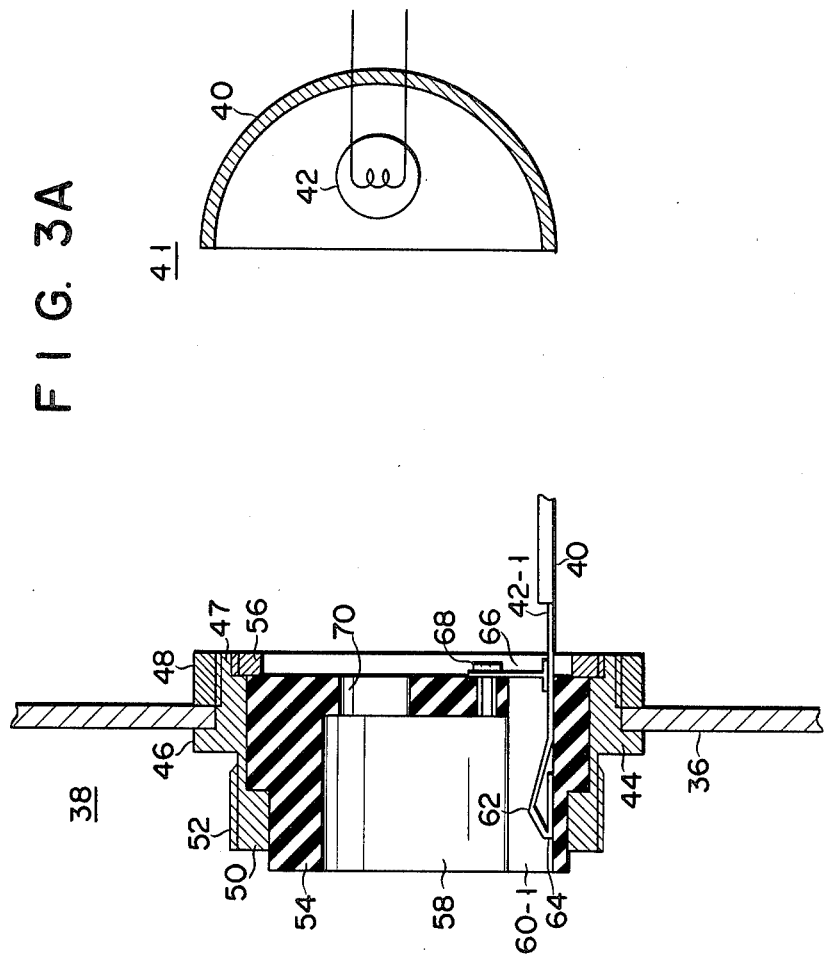

SOCKET STRUCTURE OF A LIGHT SOURCE UNIT FOR AN ENDOSCOPE SYSTEM

BACKGROUND OF THE INVENTION

The present invention relates to a socket structure of a light source unit for an endoscope system and, more particularly, a socket structure of a light source unit to which is coupled a connector or plug of a universal cord of an endoscope.

In an endoscope system, an endoscope is optically or electrically coupled to a light source unit. Therefore, a connector or plug is provided at the end of the universal cord of the endoscope. The plug of the universal cord is coupled to a socket of the light source unit. The plug has terminals connected to lines arranged in the universal cord of the endoscope and one end portion of an image guide. The socket has a recess of a shape corresponding to the outer shape of the plug and terminals to be connected to the plug terminals.

In a conventional socket, the socket terminals simply extend inward from the inner surface of a socket recess and are arranged at predetermined intervals. The adjacent terminals may be short-circuited by a finger or a member, resulting in electric shock or damage to electric units.

SUMMARY OF THE INVENTION

It is, therefore, an object of the present invention to provide a safe socket structure of a light source unit for an endoscope system which prevents electrical hazard resulting from socket terminals being touched.

In order to achieve the above object of the present invention, there is provided a socket of a light source unit for an endoscope, comprising:

a socket body made of an insulating material and having a recess, a through hole and at least one pair of slots, said recess having a shape corresponding to an outer shape of a plug to be fitted in said socket and receiving said plug therein, said through hole receiving an image guide projecting from said plug, and said at least one pair of slots receiving at least one pair of plug terminals, respectively, and extending in an insertion path of said plug terminals; and at least one pair of terminals which are respectively arranged in said at least one pair of slots, which are fixed to said socket body, and which are electrically connected to said plug terminals, respectively, when said plug is fitted in said socket.

BRIEF DESCRIPTION OF THE DRAWINGS

FIG. 1 is a schematic perspective view showing the arrangement of a conventional endoscope system;

FIG. 2 is a sectional view of a plug according to one embodiment of the present invention;

FIG. 3 is a sectional view of a socket according to one embodiment of the present invention;

FIG. 3A represents a light source;

FIG. 4 is a plan view of the socket shown in FIG. 3; and

DETAILED DESCRIPTION OF THE PREFERRED EMBODIMENT

Figure 5:
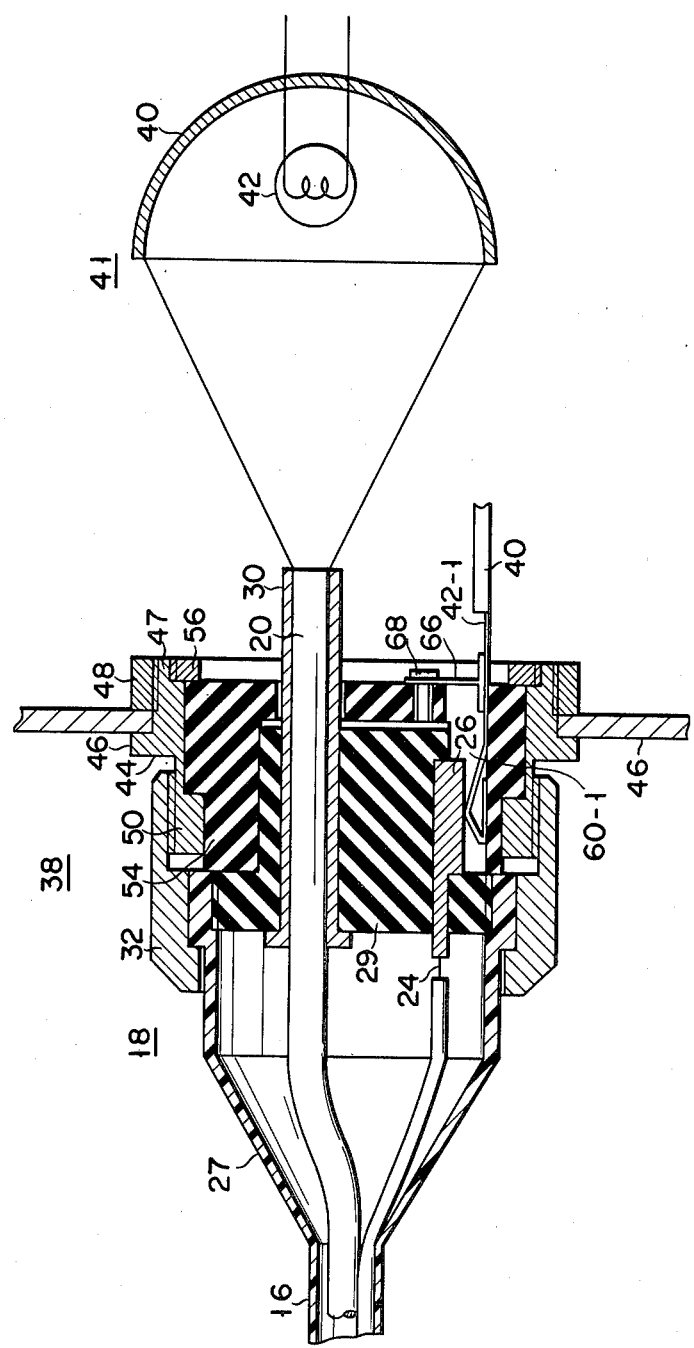
FIG. 5 is a sectional view illustrating a condition in which the plug shown in FIG. 2 is fitted in the socket shown in FIG. 3.

Referring to FIG. 1, a conventional endoscope system comprises an endoscope 2 and a light source unit 4.

As is known well, the endoscope 2 has an insertion section 6 to be inserted into a body cavity, a control section 10 for controlling the endoscope 2 to bend a bending portion 8 of the insertion section 6, and an eyepiece section 14 for allowing the operator to observe an image on a region of interest through the insertion section 6 and a light guide 20 (not shown) extending in the control section 10. A universal cord 16 extends from the control section 10 and has a plug or connector 18 at its end. The light guide 20 extends through the insertion section 6, the control section 10 and the universal cord 16. An end portion of the light guide 20 projects from the plug 18, as shown in FIG. 2. The eyepiece section 14 has a mount 22 to which a camera unit (not shown) is attachable and terminals (not shown) connected to a motor and a photometer within the camera unit when the camera unit is mounted on the eyepiece section 14. Electrical power lines and signal lines connected to the terminals extend into the plug 18 through the control section 10 and the universal cord 16. These lines are then connected to terminal rods of the plug 18, respectively. Referring to FIG. 2, one of the electrical power lines 24 is shown and is connected to a corresponding terminal rod 26.

The plug 18 has a hollow case 27 through which the light guide 20 and the electrical power line 24 extend. A plug cover 28 made of an insulator is screwed in an opening of the hollow case 27. The light guide 20 extends through the plug cover 28. A cylindrical holder 30 for protecting the light guide 20 and the terminal rod 26 are embedded in the plug cover 28. Referring to FIG. 2, the cylindrical holder 30 is projected from the end face of a cylindrical projecting portion 29 of the plug cover 28 in parallel with the central axis of the plug 18. Similarly, the surface of the terminal rod 26 which contacts with the cylindrical projecting portion 29 extends substantially parallel to the central axis of the plug 18. Further, the terminal rod 26 projects from the side surface of the cylindrical projecting portion 29. Other terminal rods (not shown) are arranged on the same circumference of the plug 18 and are embedded in the plug cover 28. Surfaces of the other terminal rods which contact with the cylindrical terminal rods 26 extend substantially parallel to the axis of the plug 18 and project from the side surface of the cylindrical projecting portion 29. A knurled fastening ring 32 is rotatably fitted around the plug hollow case 27. Threads 34 are formed on the inner surface of the fastening ring 32.

A socket 38 having a structure as shown in FIG. 3 is disposed on a front panel 36 of the light source unit 4. The light source unit 4 has a light source 41 comprising an ellipsoidal mirror 40 and a lamp 42, a power source circuit (not shown) and a photometer control circuit (not shown). The electrical power lines and the signal lines extend from the power source circuit and the photometer control circuit, respectively, to the socket 38. These lines are connected to terminal plates fixed on the sockets 38. Referring to FIG. 3, one of electrical power lines 43 is shown and is connected to a corresponding terminal plate 42-1. An attachment ring 44 is inserted into a hole formed in the front panel 36 so as to bring a flange 46 of the attachment ring 44 in contact with the front surface of the front panel 36. A ring-shaped fastening nut 48 is screwed on an annular portion 47 of the attachment ring 44 projecting from the rear surface of the front panel 36. Therefore, the front panel 36 is clamped by the flange 46 and the fastening nut 48 and the attachment ring 44 is fixed properly at the front panel 36. Threads 52 on which the fastening ring 32 is screwed are formed on an outer circumference of a ring portion 50 of the attachment ring 44 projecting outwardly from the front panel 36. An annular stepped portion is formed on the inner surface of the ring portion 50. A socket body 54 is made of an insulator and has an outer shape which corresponds to the inner shape of the attachment ring 44. The socket body 54 is fitted in the attachment ring 44. Thus, the annular stepped portion on the outer circumferential surface of the socket body 54 comes in contact with the annular stepped portion of the ring portion 50. A ring nut 56 is screwed in the annular portion 47 of the attachment ring 44 and the socket body 54 is clamped between the annular stepped portion of the ring portion 50 and the ring nut 56. The socket body 54 has a cylindrical recess or hollow 58 which corresponds to the shape of the projecting portion 29 of the plug cover 28. As shown in FIG. 4, slots 60-1, 60-2, 60-3, 60-4 and 60-5 which are open to the recess are axially formed in the socket body 54 around the axis of the socket and are substantially parallel thereto. Terminal plates 42-1, 42-2, 42-3, 42-4 and 42-5 having elastically deformable structure are received in the slots 60-1, 60-2, 60-3, 60-4 and 60-5, respectively. Vertex portions 62 of the terminal plates 42-1 to 42-5 are completely received in the slots 60-1 to 60-5, respectively. Ends 64 of the terminal plates 42-1 to 42-5 are located short of the opening end of the socket body 54. The width of the slots 60-1 to 60-5 is slightly larger than that of the terminal plates 42-1 to 42-5. The terminal plates 42-1 to 42-5 are fixed by screws 68 to the socket body 54 through bending portions 66, as shown in FIG. 3. A through hole 70 into which the cylinder holder 30 is inserted is formed in the socket body 54.

The plug 18 is fitted in the socket 38, as shown in FIG. 5. The end face of the cylinder holder 30 of the plug 18 is faced to the through hole 70 of the socket 38, and the end face of the plug cover 28 or the cylindrical projecting portion 29 is faced to the recess 58 of the socket 38. Then, the plug 18 is rotated to a predetermined position so that the cylinder holder 30 and the cylindrical projection portion 29 are inserted into the through hole 70 and the recess 58 respectively, the terminal rod 26 of the plug 18 is inserted into the corresponding slot 60-1 and other terminal rods are inserted into the corresponding slots 60-2 to 60-5, respectively. When the fastening ring 32 of the plug 18 is rotated, the threads 34 of the plug 18 are engaged with the threads 52 of the attachment ring 44 of the socket 38. Therefore, the plug 18 is fixed in the socket 38 completely. The terminal rod 26 which is inserted in the slot 60-1 comes in contact with the vertex end 62 of the terminal plate 42-1 in the slot 60-1. The terminal rod 26 is electrically connected to the terminal plate 42-1 properly. The end face of the light guide 20 within the cylindrical holder 30 inserted in the through hole 70 is located on the optical path of the light source 41. Therefore, light from the light source 41 can be guided in the light guide 20.

With the above arrangement, the plug 18 is completely and properly fixed in the socket 38. Further, when the plug 18 is detached from the socket 38, an electrical hazard resulting from the terminal plate being contacted is prevented, assuring safe operation. Even if a finger is inserted in the recess 58 of the socket 38, the terminal plates 42-1 to 42-5 are not exposed and the finger can hardly be brought into contact with the terminal plates 42-1 to 42-5 within the slots 60-1 to 60-5. Further, since the terminal plates 42-1 to 42-5 are received in the corresponding slots, respectively, and are separated from the wall of the plug body, dust or water may not cause short-circuiting of the terminal plates. Therefore, electronic components may not be damaged and electric shock can be prevented.

What is claimed is:

1. A combination of a socket and a plug of a light source unit for an endoscope, wherein said plug is made of an electrically insulating material and comprises a cylindrical projecting portion extending along the axis of said plug, a holder secured to the cylindrical projecting portion and adapted to receive a light guide of the endoscope, the axis of the holder being parallel to the axis of said plug, and plug terminals attached to the outer periphery of the cylindrical projecting portion and arranged asymmetrically with respect to the axis of said plug; and said socket comprises a socket body made of an electrically insulating material and including a recess adapted for receiving the cylindrical projecting portion, a hole extending parallel to the axis of said socket and adapted to receive the holder of said plug, slots asymmetrically arranged along the axis of said socket with respect to the axis of said socket so as to receive the plug terminals, and socket terminal placed in the slots, secured to the socket body and electrically connected to the plug terminals when said plug is inserted into said socket.

2. The combination according to claim 1, wherein said socket terminals are elastically deformable.

3. The combination according to claim 1, wherein said socket further comprises an attachment ring in which said socket body is fitted and which has, on an outer circumferential surface thereof, threads to mesh with said plug.

4. The combination according to claim 3, wherein said light source unit has a front panel, and said attachment ring is fixed to said front panel.

* * * * *